United States Patent
Tetz et al.

(10) Patent No.: US 8,094,314 B2
(45) Date of Patent: Jan. 10, 2012

(54) OPTICAL SENSING BASED ON SURFACE PLASMON RESONANCES IN NANOSTRUCTURES

(75) Inventors: Kevin Tetz, Brentwood, TN (US); Lin Pang, San Diego, CA (US); Yeshaiahu Fainman, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 478 days.

(21) Appl. No.: 12/091,051

(22) PCT Filed: Oct. 23, 2006

(86) PCT No.: PCT/US2006/041263
§ 371 (c)(1),
(2), (4) Date: Apr. 21, 2008

(87) PCT Pub. No.: WO2008/039212
PCT Pub. Date: Apr. 3, 2008

(65) Prior Publication Data
US 2008/0278728 A1  Nov. 13, 2008

Related U.S. Application Data

(60) Provisional application No. 60/729,160, filed on Oct. 21, 2005.

(51) Int. Cl.
*G01N 21/55*  (2006.01)
(52) U.S. Cl. .................................................. 356/445
(58) Field of Classification Search .................. 356/445; 250/286–287
See application file for complete search history.

(56) References Cited

U.S. PATENT DOCUMENTS

| 5,229,833 A * | 7/1993 | Stewart ......................... 356/364 |
| 5,255,075 A * | 10/1993 | Cush ............................. 356/445 |
| 5,846,843 A * | 12/1998 | Simon ........................... 436/527 |
| 5,952,035 A * | 9/1999 | Erb et al. ..................... 427/2.11 |
| 6,331,276 B1 * | 12/2001 | Takei et al. ................. 422/82.09 |
| 6,462,809 B1 * | 10/2002 | Ryan et al. .................... 356/128 |
| 6,818,907 B2 | 11/2004 | Stark |
| 6,930,057 B2 | 8/2005 | Saito et al. |
| 2001/0040130 A1 * | 11/2001 | Lorch et al. .................. 210/601 |
| 2003/0087290 A1 * | 5/2003 | Tarlov et al. ...................... 435/6 |
| 2003/0132392 A1 * | 7/2003 | Kuroda et al. ............... 250/397 |
| 2004/0130723 A1 * | 7/2004 | Yager et al. .................. 356/445 |
| 2004/0218249 A1 * | 11/2004 | Kochergin ................... 359/280 |
| 2005/0105091 A1 * | 5/2005 | Lieberman et al. .......... 356/369 |

(Continued)

FOREIGN PATENT DOCUMENTS
WO  WO 2008/039212  4/2008

OTHER PUBLICATIONS

Gordon, R et al., Strong Polarization in the Optical Transmission through Elliptical Nanohole Arrays, Jan. 23, 2004, Physical Review Letters, vol. 92, No. 3, pp. 037401-1 thru 037401-4.*

(Continued)

*Primary Examiner* — Tarifur Chowdhury
*Assistant Examiner* — Michael P Lapage
(74) *Attorney, Agent, or Firm* — Perkins Coie LLP

(57) ABSTRACT

Devices and techniques for using nanostructures such as nanohole metal films to construct SPP sensors for sensing various substances.

46 Claims, 1 Drawing Sheet

U.S. PATENT DOCUMENTS

2006/0072114 A1* 4/2006 Sigalas et al. .................. 356/445

OTHER PUBLICATIONS

Altewischer et al., "Polarization analysis of propagating surface plasmons in a subwavelength hole array," J. Opt. Soc. Am. B. 20(9): 1927-1931 (Sep. 2003).

Barnes et al., "Photonic surfaces for surface-plasmon polaritons," J. Opt. Soc. Am. A 14(7): 1654-1661 (1997).

Barnes et al., "Physical origin of photonic energy gaps in the propagation of surface plasmons on gratings," Physical Review B 54(9): 6227-6244 (1996).

Barnes et al., "Surface plasmon polaritons and their role in the enhanced transmission of light through periodic arrays of subwavelength holes in a metal film," Phyiscal Review Letters 92(10): 107401-1 to 107401-4 (Mar. 2004).

Barnes et al., "Surface plasmon subwavelength optics," Nature 424: 824-830 (Aug. 14, 2003).

Brolo et al., "Surface Plasmon Sensor Based on the Enhanced Light Transmission through Arrays of Nanoholes in Gold Films," Langmuir 20: 4813-4815 (2004).

Bryan-Brown, G.P., and J.R. Sambles, "Polarisation conversion through the excitation of surface plasmons on a metallic grating," Journal of Modern Optics 37(7): 1227-1232 (1990).

Cao, Q. and P. Lalanne, "Negative Role of Surface Plasmons in the Transmission of Metallic Gratings with Very Narrow Slits," Phyiscal Review Letters 88(5): 057403-1to 057403-4 (Feb. 4, 2002).

Ditlbacher et al., "Two-dimensional optics with surface plasmon polaritons," Applied Physics Letters 81(10): 1762-1764 (Sep. 2, 2002).

Dykhne et al., "Resonant transmittance through metal films with fabricated and light-induced modulation," Physical Review B 67: 195402-1 to 195402-13 (2003).

Ebbesen et al., "Extraordinary optical transmission through subwavelength hole array," Nature 391: 667-699 (Feb. 12, 1998).

Fano, U., "Effects of Configuration Interaction on Intensities and Phase Shifts," Physical Review 124(6): 1866-1878 (Dec. 15, 1961).

Genet et al., "Fano-type interpretation of red shifts and red tails in hole array transmission spectra," Optics Communications 225: 331-336 (2003).

Ghaemi et al., "Surface plasmons enhance optical transmission through subwavelength holes," Physical Review B 58(11): 6779-6782 (Sep. 15, 1998).

Goto et al., "Propagation loss measurement for surface plasmon-polariton modes at metal waveguides on semiconductor substrates," Applied Physics Letters 84(6): 852-854 (Feb. 2004).

Hensley, P. and L.M. Smith, "Analytical biotechnology, editorial overview," Current Opinion in Biotechnology 8: 1-5 (1997).

Homola et al., "Surface plasmon resonance sensors based on diffraction grating and prism couplers: sensitivity comparison," Sensors and Actuators B54: 16-24 (1999).

Homola et al., "Surface plasmon resonance sensors: review," Sensors and Actuators B54: 3-15 (1999).

Lamprecht, B. et al., "Surface plasmon propagation in microscale metal stripes," Applied Physics Letters 79(1): 51-53 (Jul. 2, 2001).

Lezec, H.J. et al., "Beaming Light from a Subwavelength Aperturen," Science 297: 820-822 (Aug. 2, 2002).

Maier et al., "Plasmonics- A Route to Nanoscale Optical Devices," Adv. Mater. 13(19): 1501-1505 (Oct. 2, 2001).

Martín-Moreno, L. et al., "Theory of Extraordinary Optical Transmission through Subwavelength Hole Arrays," Physical Review Letters 86(6): 1114-1117 (Feb. 5, 2001).

Nezhad et al., "Gain assisted propagation of surface plasmon polaritons on planar metallic waveguides," Optics Express 12(17): 4072-4079 (Aug. 23, 2004).

Rokitski et al., "Propagation of Femtosecond Surface Plasmon Polariton Pulses on the Surface of a Nanostructured Metallic Film: Space-Time Complex Amplitude Characterization," Physical Review Letters, vol. 95, pp. 177401-1 to 177401-4, Oct. 2005.

Rokitski et al., "Study of spatial-temporal characteristics of optical fiber based on ultrashort-pulse interferometry," Optics Letters 26(15): 1125-1127 (Aug. 1, 2001).

Sarrazin, M. et al., "Role of Wood anomalies in optical properties of thin metallic films with a bidimensional array of subwavelength holes," Physical Review B. 67: 085415-1 to 085415-8 (2003).

Steele, J.M. et al., "Metallodielectric grating with subwavelength slots: Optical properties," Physical Review B 68: 205103-1 to 205103-7 (2003).

Tetz et al., "Characterization of surface plasmon polariton pulse propagation on thin metallic films and two dimensional nanohole arrays," Lasers and Electro-Optics Society, 2005. LEOS 2005. The 18th Annual Meeting of the IEEE, Oct. 22-28, 2005 pp. 158-159 (2005) ISBN: 0-7803-9217-5.

Tetz et al., "Excitation and direct imaging of surface plasmon polariton modes in near-infrared," Lasers and Electro-Optics Society, 2004. LEOS 2004. The 17th Annual Meeting of the IEEE, Nov. 7-11, 2004, vol. 2, pp. 947-948 ISBN: 0-7803-8557-8.

Tetz et al., "Excitation and direct imaging of surface plasmon polariton modes in a two-dimensional grating," Applied Physics Letters 86(11): 111110-1 to 111110-3 (2005).

Zayats, A. V. and I.I. Smolyaninov, "Near-field photonics: surface plasmon polaritons and localized surface plasmons," Journal of Optics A: Pure and Applied Optics 5: S16-S50 (2003).

Zhu, H. and M. Snyder, "Protein chip technology," Current Opinion in Chemical Biology 7: 55-63 (2003).

Tetz, et al., "High-resolution surface plasmon resonance sensor based on linewidth-optimzed nanohole array transmittance," Optics Letters, 31(10):1528-1530, May 2006.

* cited by examiner

OPTICAL SENSING BASED ON SURFACE PLASMON RESONANCES IN NANOSTRUCTURES

RELATED APPLICATION

This application claims the benefit of U.S. Provisional Application No. 60/729,160 entitled "OPTICAL SENSING BASED ON SURFACE PLASMON RESONANCES IN NANOSTRUCTURES" and filed on Oct. 21, 2005, which is incorporated by reference in its entirety as part of the specification of this application.

GOVERNMENT FUNDING

The research and development for inventions described in this application received funding from the U.S. Government under DAF/Air Force Grant No. FA9550-04-1-0417 and NSF Grant No. ECS-0403589. The U.S. Government have rights to various technical features described in this application.

BACKGROUND

This application relates to optical sensing including optical sensing of chemical and biological substances.

Plasmons are eigenmodes of collective density oscillations of quasi-free electrons or an electronic gas in metals and other materials under optical excitation. Plasmons are generated by coupling photons and electrons at or near a surface of an electrically conductive material and thus are sometimes referred to as surface plasmon polaritons (SPPs). The coupling of the photon and electron gas can lead to effective binding energy or a momentum mismatch which precludes coupling of a free space photon to the SPP in normal circumstances. Typically, an incident photon needs some additional momentum to excite a SPP under a phase-matched surface plasmon resonance (SPR) condition.

Surface plasmon polaritons have been extensively studied and some recent work has explored their potential for building various integrated optical devices. The intrinsic mode confinement in SPPs, due to their surface nature, may have potential advantages for building sub-diffraction limited waveguides and in facilitating full three-dimensional optical confinement. Further interest has been sparked by the observation that SPP waves can enhance optical transmittance through optically thick metallic films with sub-wavelength features. The radiated diffraction pattern by excited SPPs can be controlled to operate an SPP device as nano-antennae and transmitters.

Surface plasmon resonance sensors can be constructed for biological and chemical sensing. Many SPR sensors use a metal-dielectric interface and a prism to excite SPP waves via the Kretschmann configuration based on optical evanescent coupling through the prism. In such a SPR sensor, a metallic film is the interrogation medium and is placed or deposited on the prism. The effective numerical aperture of this prism-based system is limited and this further limits the spatial resolution and resolvable spots. In order to meet the SP resonance for a planar metallic film, typical illumination conditions are set at a relatively large angle and this configuration can impose server constraints on the depth of focus in imaging of the system. The limited depth of focus in imaging can be unsuitable for large arrays of assays. In addition, the lateral resolution of the prism-based SP system can be limited by the finite SPP propagation length and are unsuitable for massive parallelization of such SPR sensors.

In 1998, T. E. Ebbessen et al. designed sub-wavelength nanohole arrays in metallic films to produce "extraordinary optical transmission" through such sub-wavelength nanoholes based on excitation of SPPs. See, e.g., Ebbesen et al., Extraordinary Optical Transmission through Sub-Wavelength Hole Arrays, Nature, vol. 39, 667, 669 (1998) and Ghaemi et al., Surface Plasmon Enhance Optical Transmission through Subwavelength Holes, Physical Review, Vol. 58, No. 11, 6779, 6782 (1998). Such nanohole arrays exhibit interesting SPP properties and can be potentially used in various applications.

SUMMARY

This application describes, among others, devices and techniques for using nanostructures such as nanohole metal films to construct SPP sensors for sensing various substances.

In one implementation, an optical sensing device includes a nanohole array comprising a substrate and a metal layer formed on the substrate to include an array of holes arranged in a periodic two-dimensional pattern and to be in contact with a sample under measurement. Each hole has a dimension less than one wavelength of probe light to which the nanohole array is responsive to produce surface plasmons at an interface of the metal layer and the sample under a surface plasmon resonance condition. This device includes an input optical module to direct a collimated input optical probe beam at the wavelength of the probe light to the nanohole array. The input optical module includes an optical polarization control unit operable to control an input optical polarization of the collimated input optical probe beam incident to the nanohole array. An output optical module is also included in this device to receive an optical output produced by the surface plasmons at the interface between the metal layer and the sample. The output optical module includes an output optical polarizer to select light in the optical output at a selected output polarization for optical detection.

In one implementation, an optical sensing method is described to provide a nanohole array comprising a metal layer and an array of holes arranged in a periodic two-dimensional pattern to be in contact with a sample under measurement. Each hole has a dimension less than one wavelength of probe light to which the nanohole array is responsive to produce surface plasmons at an interface of the metal layer and the sample under a surface plasmon resonance condition. A collimated input optical probe beam at the wavelength of the probe light is directed to the nanohole array under the surface plasmon resonance condition to excite surface plasmons at the interface of the metal layer and the sample. The light in an optical output produced by the surface plasmons at the interface between the metal layer and the sample in a selected output polarization is into a camera. The image captured by the camera is processed to extract information of the sample. The input polarization of the collimated input optical probe beam and the selected output polarization for the light captured by the camera may be controlled to be orthogonal to each other to produce a Lorentzian spectral profile in the light captured by the camera.

In another implementation, an optical sensing device includes a nanohole array comprising a metal layer with a two-dimensional array of holes configured to interface with a sample under measurement and to support surface plasmon under excitation of probe light, an input polarization control unit to control input polarization of an input optical probe beam of the probe light incident to the nanohole array, and an output optical polarizer to receive signal light which is transmission of the input optical probe beam through the nanohole array and the sample to select a polarization of the signal light for optical detection. Each hole has a dimension less than one wavelength of the probe light and the input polarization control unit and the output optical polarizer are configured to be orthogonal to each other in polarization.

In yet another implementation, an optical sensing device includes a substrate, a metal layer formed on the substrate and patterned to comprise a two-dimensional array of holes configured to interface with a sample under measurement and to support surface plasmons under excitation of probe light, and microfluidic channels formed in contact with the metal film. Each microfluidic channel supports a respective fluid sample under measurement and each hole has a dimension less than one wavelength of the probe light.

Implementations of SPP sensors described can use polarization control in the optical input and optical output of a nanohole metal film to produce a spectrally narrow transmission profile to allow for high resolution detection. As an example, a SPP sensor can include a nanohole array with a metal layer configured to support surface plasmon under excitation of an input optical probe beam; an input polarization control unit to control input polarization of the input optical probe beam incident to the nanohole array; and an output optical polarizer to receive optical transmission from the nanohole array and to select a polarization of the transmission beam for optical detection. The input polarization control unit and an output optical polarizer are controlled to produce a Lorentzian spectral profile of the transmission beam through the output optical polarizer.

These and other implementations are described in detail in the attached drawings, the detailed description and the claims.

BRIEF DESCRIPTION OF DRAWINGS

FIGS. 2, 3, 4A, 4B, 5A and 5B show examples of nanohole arrays suitable for use in FIG. 1.

FIG. 6 shows an example of the device in FIG. 1.

FIG. 7 shows measured salt concentration using an optical sensing device based on the design in FIG. 1.

FIG. 8 shows an example of a nanohole array in an isotropic 2-dimensional array and the phase matching condition for the surface plasmon resonance.

FIG. 9 Normalized transmission as a function of (A) energy (wavelength) and (B) parallel wave vector (angle). In each case the dotted lines correspond to the PP and the solid lines the OP polarization states (as illustrated in FIG. 1 and described in the text). The transmission in each case has been normalized to the maximum to clearly illustrate the respective lineshape functions. Also inset in FIG. 2b is the same data plotted in logarithmic scale to show the ~15-20 dB background level reduction for the Lorentzian vs Fano-type resonances.

FIG. 10 shows measurements for resonance peak position shift versus refractive index change (i.e. salt concentration in water) in the fluidic overlayer. The black line is a linear fit to the datum. Shaded regions correspond to approximate peak position (absolute refractive index) errors in the fitting procedure for the OP and PP conditions for both air and water broadened linewidths as well as estimated theoretical resolution limits.

FIGS. 11A and 11B show unpolarzied spectral measurements of unpolarized zero-order for cubic arrays of holes in an thin aluminum film on a GaAs substrate, and calculated SPP phase matching conditions for the same parameter space, respectively. Data from several arrays with different periods a have been combined for these composite intensity images, where the stitching frequencies appear as horizontal white lines. The transmittance has been normalized by the hole area per unit cell. Also shown is a small box indicating the frequency/wavevector region studied with high resolution.

FIGS. 12A and 12B shows measured transmittance as a function of frequency (radial direction) and analyzer angle (azimuthal angle).

DETAILED DESCRIPTION

Figure 1:
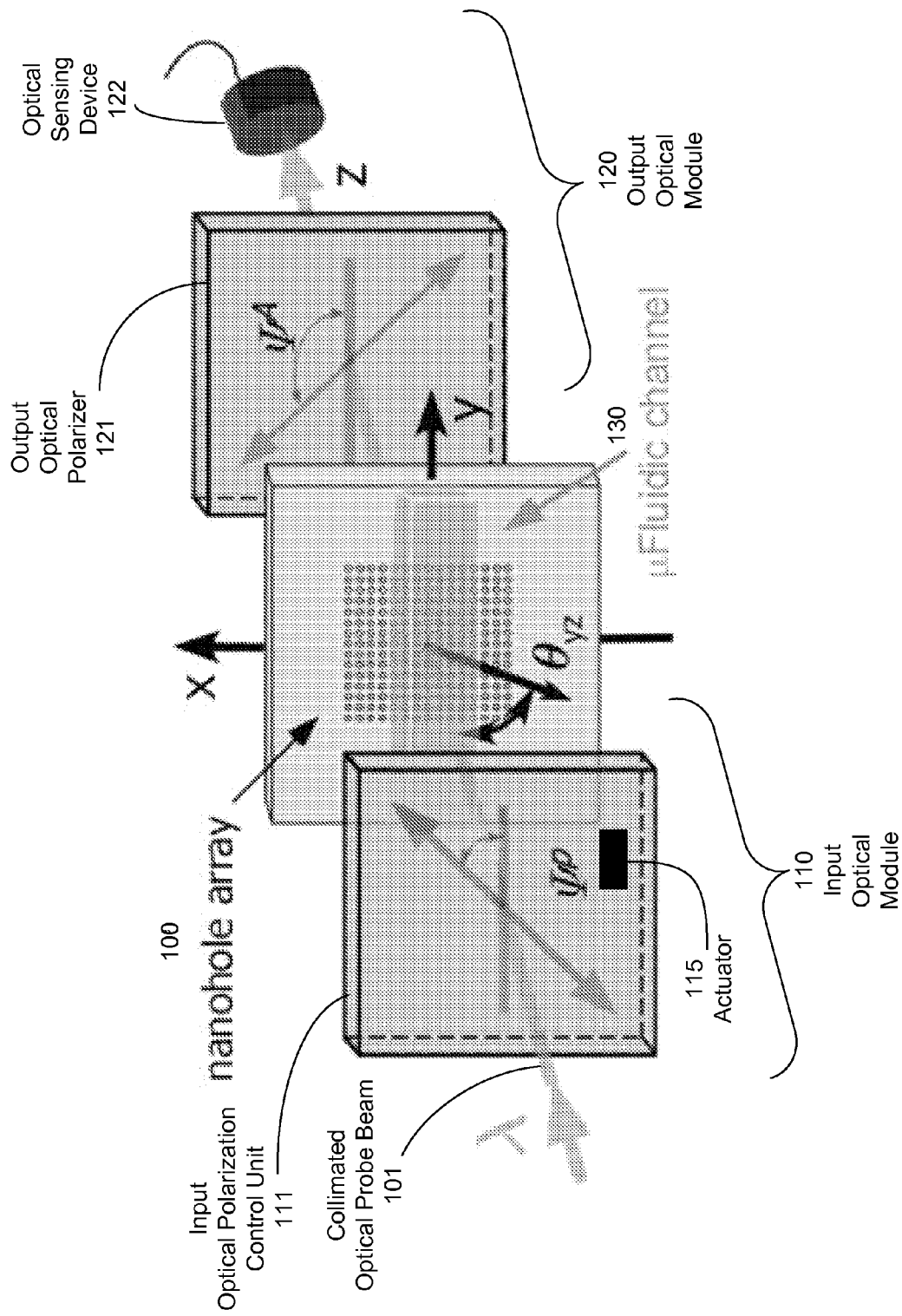
FIG. 1 shows one exemplar implementation of an optical sensing device using a collimated optical probe beam and a nanohole array.

FIG. 1 shows one example of an optical sensing device that uses a nanohole array. This optical sensing device includes a nanohole array 100, an input optical module 110 and an output optical module 120 that are optically aligned to from an optical train. The nanohole array 100 includes a substrate and a metal layer formed on the substrate to include an array of holes arranged in a periodic two-dimensional pattern. The metal layer is in contact with a sample under measurement to form a metal-sample interface that supports surface plasmons. Each hole has a dimension less than one wavelength of probe light to which the nanohole array is responsive to produce surface plasmons at the metal-sample interface under a surface plasmon resonance condition. More details on the nanohole array 100 are provided below. The input optical module 110 is designed to direct a collimated input optical probe beam 101 at the wavelength of the probe light to the nanohole array 100 and includes at least an optical polarization control unit 111 to control an input optical polarization of the collimated input optical probe beam 101 incident to the nanohole array 100. The optical polarization control unit 111 can be implemented in various configurations, such as a fixed or adjustable optical polarizer or a multi-element optical polarization controller. The input optical module 110 can also include a light source that generates the light for the collimated input optical probe beam 101 and an optical collimator to collimate the light from the light source, thus producing the collimated input optical probe beam 101. This use of a collimated probe beam limits the optical wavevector of the probe light at a single, known value and allows the signal generated by excited surface plasmons at the metal-sample interface to be processed to extract information of the sample under measurement. The output optical module 120 is used to receive the optical output produced by the excited surface plasmons at the metal-sample interface and includes an output optical polarizer 121 to select light in the optical output at a selected output polarization for optical detection. An optical sensing device, such as an optical detector array, can be used to capture the optical output and an optical imaging unit such as an imaging lens assembly can be used to image the metal-sample surface to the optical sensing device.

The surface plasmon resonance condition at the metal-sample interface of the nanohole array 100 can be controlled by a number of parameters, such as the input optical polarization, the optical wavelength of the collimated optical probe beam 101, the amplitude of the electric field or the optical power level of the collimated optical probe beam 101, and the incident angle of the collimated optical probe beam 101. A tunable light source can be used as part of the input optical module 110 to tune the optical wavelength of the probe light. This can be implemented in various configurations. A tunable laser, for example, may be used. As another example, a broad spectral light source and an optical filter can be combined to produce the probe light at a desired probe wavelength. The incident angle of the collimated optical probe beam 101 can be controlled by controlling the relative orientation between the input optical module 110 and the nanohole array 100. A positioning stage can be used to hold the nanohole array 100 and to adjust the orientation of the nanohole array 100 relative to the collimated optical probe beam to achieve a desired surface plasmon resonance condition for a given sample under measurement. An actuator 115 can also be provided in the input optical module 110 to control the angle of the collimated optical probe beam 101 relative to the fixed nanohole array 100.

The incident angle of the collimated optical probe beam 101 can be controlled at the normal or near normal incidence to achieve a desired surface plasmon resonance condition. The optical readout of the nanohole array 100 is selected to be the 0-order diffraction mode produced by the periodic structure of the nanoholes. This configuration can be used to provide optical sensing over a large sample area on the nanohole array 100, high resolution imaging, and a large number of simultaneous measurements. The nanoholes in a 2-dimensional periodic pattern as optical scattering elements can be used to reduce the SP propagation length to allow for a dense packing of sensing elements and thus reduces the amount of analyte material needed for a given measurement. This property in turns permits multiple parallel microfluidic channels with different fluidic samples and different sample areas functionalized with different biomolecular recognition elements are implemented on a nanohole array. The control of the input polarization in exciting the SPR and the output polarization for readout of the SPR signal can be used to reduce the spectral linewidth and hence enhance the sensitivity of the instrument.

In FIG. 1, a microfludic channel 130 is shown and placed in contact with the metal film of the nanohole array to guide a fluid sample. Two or more such microfluidic channels can be used to supple different fluid samples to the nanohole array 100 for measurement. Microfluidic channels can be parallel channels that are fabricated over the metal film. A microfluidic channel can be formed either directly on the metal film or on a thin overlayer (e.g., SiO2) which is directly formed on the metal film. A polymer material, such as Polystyrene-b-polydimethyl siloxane (PDMS), can be used to form a microfluidic channel. A microfluidic channel may be a PDMS microfluidic molded structure and can be bonded to the metal film. Alternative to the polymer molding, photolithography can be used to fabricate a microfluidic channel on a substrate. A microfluidic channel can be used to minimize the amount of the analyte needed for a measurement.

FIG. 2 shows a cross section of an exemplary nanohole array 100 formed on a substrate 210 and a patterned metal film 220. The patterned metal film 220 is deposited on the substrate 210 and is patterned to have 2-dimensional nanoholes in row and columns. The exposed surface of the metal film 220 can be functionalized to include a layer of a biomolecular recognition element 230 for binding with certain target particles in a fluid sample 240 that is in contact with the metal film 220. In addition, the fluid sample 240 may be fluorescently tagged using one or more molecular tags. Various fluorescent molecule labeling techniques can be applied to the nanohole array devices described in this application. Such fluorescent labeling can provide a higher degree of confidence in certain sensing applications. In some applications, a single fluorescent tag is sufficient to provide the desired specificity. In some other applications, two different fluorescent tags may be used at the same time.

The nanohole array 100 in FIG. 1 can be designed to include two or more different sample areas with different biomolecular recognition elements for simultaneous measurements. FIG. 3 shows an example of such a nanohole array that has different sample areas each having an array of 4×4 nanoholes. The collimated optical probe beam 101 can be used to illuminate an area covering two or more adjacent sample areas for simultaneous measurements. In addition, the input optical module 110 in FIG. 1 can be designed to produce different collimated optical probe beams to simultaneously illuminate different areas of the nanohole array 100.

The nanoholes in the nanohole array 100 can be made in various configurations. FIGS. 4A and 4B show an example where the nanoholes are symmetric circular holes with a diameter of 400 nm. FIGS. 5A and 5B show another example where the nanoholes are spatially anistropic in shape, e.g., elliptical. In addition, nanoholes can be through nanoholes that penetrate through the metal film or non-through nanoholes that penetrate a part of the metal film without completely penetrating through the metal film. A metal film with non-through nanholes physically separates the sample from the substrate on which the metal film is formed and such separation can be beneficial in various devices.

The optical sensing device in FIG. 1 can allow an optical transmission through the metal film and the sample that is produced by the surface plasmons at the interface between the metal layer and the sample. In this design, the input and output optical modules 110 and 120 are located relative to the nanohole array 100 to direct the collimated input optical probe beam 101 to the nanohole array 100 and to receive the optical output from the nanohole array 100, respectively, on opposite sides of the nanohole array. Alternatively, the optical output produced by the surface plasmons at the interface between the metal layer and the sample is an optical reflection by the metal film so that the input and output optical modules 110 and 120 are located relative to the nanohole array 100 to direct the collimated input optical probe beam 101 to the metal film of the nanohole array 100 and to receive the optical output reflected from metal film of the nanohole array 100 on a common side of the nanohole array 100.

FIG. 6 shows an example implementation of the optical sensing device in FIG. 1 in the optical transmission mode. A laser or lamp 114 is provided as part of the input optical module 110 to produce the probe light. A fiber 113 is used to guide the probe light from the light source 114 to a collimator lens 112 which collimates the output light from the fiber 113 to produce the collimated probe beam 101. The input polarization control unit 111 in this example includes two polarizers and a quarter wave plate located between the two polarizers. A nanohole array stage 103 is used to hold the nanohole array and to provide angular adjustments along two orthogonal axes to control the incident direction of the collimated optical probe beam 101. The output optical module 120 includes two imaging lenses 123 and 124 in a 4f configuration to image the nanohole array 100 onto a camera 122. The imaging lens 123 close to the nanohole array 100 may be a microscope lens with a focal length f shorter than the focal lens F of the second imaging lens 124. As an option, a quarter wave plate or a liquid crystal modulator 125 may be placed between the nanohole array 100 and the output optical analyzer 121 to control the polarization received at the output optical analyzer 121.

Implementations of SPP sensors described here use polarization control in the optical input and optical output of a nanohole metal film to produce a spectrally narrow transmission profile to allow for high resolution detection. The techniques described here may also be used to ease the fabrication tolerances on the device structure and allow for low-cost, feasible device fabrication. The optical sensing can be achieved by optically detecting miniscule changes in the local effective index of refraction at the interface with the metal film through monitoring surface plasmon mediated transmission through, or reflection from, nanohole arrays in thin metallic film. Therefore, the devices described here can be used as a generic sensor platform for a wide range of optical sensing applications, including chemical and biological sensing applications. Notably, the input polarization of the probe light and the polarization of the output optical polarizer can be specifically controlled to control the spectral profile of the transmission as a well-defined narrow line shape such as a Lorentzian line shape when the input polarization and output polarization are orthogonal to each other. The polarization of such an SSP sensor is not properly controlled, the spectral lineshape may be a Fano type profile which has a poor spectral resolution in comparison with a Lorentzian profile.

FIG. 7 shows an example measurement of NaCrO4 concentration in a salt fluid sample using the sensing device in FIG. 1 in a cross polarization configuration to achieve the Lorentzian spectral profile in the output. An initial measurement can be obtained in the nanohole array without the salt fluid sample and then another measurement can be obtained in presence of the salt fluid sample. The shift in the SPR condition can be used to extract the information on the concentration of NaCrO4 and some experiment data shows that a change in the refractive index of about $10^{-5}$ can be directly measured.

The polarization-selective sensors described in this application can be designed to use the SPP mediated transmission through the nanohole arrays. High resolution imaging can be easily accomplished with interrogation occurring at normal or near normal incidence, and the resonance shift may be read out with wavelength, amplitude, angular or, with careful design, by phase sensitive interrogation methods. The nanohole array radiatively damps the SPP wave, and hence enables more compact integration. The transmittance resonance through the nanoholes is monitored for a particular polarization state of the incident field, and is analyzed with a second polarizer in such a way as to minimize evanescent tunneling through the subwavelength apertures. This configuration, in effect, minimizes coherent interference effects in structures that have reasonable feature sizes (~100 s nm) and aspect ratios—and are therefore amenable to high-throughput, large area fabrication techniques.

In addition, the large field enhancement is useful in SERS, SECARS, and other sensitive nonlinear spectroscopy methods. Design of a nanoscale metallic nanostructure that enables both linear sensing—for high throughput—and nonlinear—for specificity and interrogation of specific reactions—will prove to be a significant advance over other technologies. The far-field transmission is significantly enhanced due to the enhanced surface fields under the SPR condition and such far-field spectroscopic measurements can be used to map the effective SPP dispersion. We have shown the distinctive polarization dependence of the arrays and used this property to separate SPP mediated transmission mechanisms from the evanescent tunneling through a waveguide below cutoff. With knowledge of the SPP dispersion, we further have demonstrated methods for exciting and imaging SPP modes both in and between these nanohole arrays, again using the polarization properties of the excitation, in this case space variant, to enable this novel, simple imaging technique. Sensing can also be achieved by SPP wavepackets using femtosecond laser pulses. Femtosecond spatial heterodyne imaging has also been utilized to investigate the ultrafast SPP dynamics in both amplitude and phase. These studies have led to new understanding of the nature of the phase matching and leading to our ability to control and detect the phase and the amplitude of the SPP field distributions. Consequently, we are able to perform focusing of such SPP fields in the transverse direction.

FIG. 8 shows an example of a nanohole metal film structure that can be used as the sensing part of the SPP sensor to interface with a material to be measured. A Cartesian coordinate system is shown to illustrate the SPR condition. The lattice diagram in the reciprocal space for the special structure of the periodic nanoholes is shown in the insert. Surface plasmon polaritons (SPPs) are resonantly excited on these grating arrays. The excitation is dependent upon the frequency, wavevector, and polarization state of the incident excitation. Phase matching for the SPP waves is described by $$\vec{k}_{SP} = \vec{k}_{//} \pm i\vec{K}_G^x \pm j\vec{K}_G^{y},$$

where $\vec{K}_{//} = \vec{K}_x + \vec{K}_y = k_0[\hat{x} \sin\theta \cos\phi + \hat{y}\sin\theta \sin\phi]$ is the in-place component of the common wavevector of the collimated probe beam. It is assumed that the dimension of each nanohole (d) is much less than the spatial period (a) of the nanohole array: d<<a and that there is no coupling between adjacent sides. The resonance condition is:

$$|\vec{k}^{sp}_{1-2,2-3}| \approx k_0 \sqrt{\frac{\varepsilon_{1,3}\varepsilon_2}{\varepsilon_{1,3} + \varepsilon_2}}.$$

A small perturbation in the sample in contact with the metal layer and, in particular, any change at the interface between the metal layer and the adjacent sample causes a shift in this resonance position.

The SPR resonance linewidth depends on both radiative damping and material damping and thus can lead to a broad spectral linewidth. As described above, the input and output polarizations of an SPR sensor can be controlled to reduce the transmission linewidth and hence enhance the spectral resolution while operating in a regime that facilitates high SBP imaging. A specific example is provided below.

Samples for our experiments are fabricated by depositing gold films of ~200 nm on glass substrate followed by spin coating and patterning by holographic lithography to achieve large usable areas (~1 cm$^2$). Multiple exposures of a chemically amplified negative resist (SU-8) yields a 2-D array of nanoholes, and the exposure time and post-exposure baking step allow fine control of the hole diameter (~200 nm). To facilitate large SBP imaging, the period a of the array to be close to the wavelength λ of the excitation field (a/λ~1) with the fabricated value of a=1.4 μm. The developed SU-8 is used as a mask for etching nanoholes into the gold film using ICP/RIE dry etching, and a PDMS mold with microfluidic delivery channel 1 cm×2 mm×100 μm is then bonded to the substrate by oxygen plasma.

An apparatus based on the device design in FIG. 1 is used to conductor the measurements. The input and output polarization states of a tunable laser are controlled to provide the variable spectral or angular Fano-type profiles. A microfludic channel is used to transport the analyte fluid to the surface of the sensing area of the nanohole array and can be used to control the refractive index on the metal-dielectric interface to tune the SPP resonance frequency. Measurements are carried out using a collimated, tunable laser source (1520-1570 nm) of about ~1 cm in diameter is used to excite an SPP field in the 2-D nanohole array. The sample is inserted between a polarizer-analyzer pair and the transmitted light is used to simultaneously image an area of ~200×200 μm of the sample onto a CCD camera for alignment as well as onto InGaAs photodiode for transmission measurements. Angular interrogation is achieved using a mechanical rotation stage rotating the sample in the y-z plane.

For comparison, two polarization states are used in measurements: 1) parallel polarizer-analyzer (PP): polarizer and analyzer axes are parallel and oriented at $+\pi/4$ with respect to the [0,1] direction of the nanohole array (see FIG. 1) yielding equal electric field amplitudes in the x- and y-directions, and 2) orthogonal polarizer-analyzer (OP): polarizer (analyzer) axis is oriented at $+\pi/4$ ($-\pi/4$) with respect to the [0,1] direction. Resonant transmittance through the 2D nanohole array depends on the interrogation angle and the wavelength of radiation and typically has a Fano-type lineshape for PP and a Lorentzian shape for OP. There have been a number of studies that have investigated and explained the effects of the various geometric parameters on the shape of the resonant transmission (e.g., hole size, metal film thickness, and optical properties of the metal), and we note that the critical feature (assume a relatively "thick" film) is the hole diameter, which increases the scattering rate and hence broadens the resonance linewidth. This resonant transmission mechanism involves coupling to an SPP mode, evanescent transmission through the below-cutoff waveguide hole, and scattering of radiation again from the hole array to produce propagating free space modes. The surface wave is excited by a projection of the incident electric field polarization in the propagation direction, and the reradiated field is again projected onto the analyzer.

FIG. 9 shows normalized transmittance spectra for both wavelength and angular interrogation in the vicinity of [0, −1] type SPP modes with an air overlayer. A characteristic Fano shape for PP (dotted lines) and a pure Lorentzian shape for OP (solid) are observed. In the OP configuration, the background contribution is suppressed leaving only the resonance component of the transmission. The absolute transmittance is low, −23 dB (0.50%) for PP, due to the small size of the diameter of the holes (thus yielding relatively narrow lines), and drops to about −29 dB (0.13%) for OP due to additional polarization projection onto the analyzer. Ideally the extinction ratio would be limited by that of the polarizers (typically −60 dB), but in practice we measure ~15-20 dB which we attribute to depolarization due to surface roughness in the etched holes. Under wavelength interrogation the background level does not drop to the same deep minimum levels within the tuning range of our laser. The measured full-width-half-maxima (FWHM) for wavelength interrogation (FIG. 9A) are 1.28 meV (2.47 nm) and −2.86 meV (5.53 nm) for OP and PP, respectively, and the PP transmission peak is red-shifted from that in OP by 0.40 meV (0.77 nm). Similarly, the measured FWHM for angular interrogation (FIG. 9B) are 0.0012 a$k_{//}/2\pi$(0.092°) and 0.011 (0.87°) for OP and PP, respectively, and the corresponding peak shift is 0.0005 (0.04°).

Next we explore the resonant transmission through 2D nanohole array for sensor applications by introducing an index-calibrated solution through the microfluidic channel to create a controlled gold-fluid interface. We repeat our experiments on angular and wavelength interrogation exciting the [0, +1] type SPP modes and vary the refractive index of the overlayer fluid (varying concentrations of $Na_2CrO_4$ in $H_2O$). Since the resolving power and interrogation range are both higher, we focus our following study on angular interrogation.

FIG. 11 shows experimental results on position of the resonant transmission peak through angular interrogation as a function of the change in the index of refraction of the fluid on the interface. Due to the strong absorption of water in this wavelength range, the linewidths for wavelength and angular interrogation broaden to values of 4.32 meV (8.31 nm) and 0.0064 a$k_{//}/2\pi$(0.52°), respectively, with OP. At shorter wavelengths the damping due to water is reduced—however the metal losses are larger. Also, at shorter wavelengths there is a greater mode overlap of the resonant field with the reaction of interest as the extent of the mode into the dielectric is reduced. We note that one may well monitor another position on this curve, for example the point of highest slope in the PP (at approximately the SPP resonance position), but by usual convention we monitor the resonance maxima. Error bars in the horizontal direction are from uncertainty in the solution index of refraction as well as possible variations in temperature. Peak positions are determined by both the method of moments (centroid position) and by fitting Lorentzian functions, and the error bounds for these methods in the presence of noise are shown as the various shaded regions. This procedure corresponds to estimated sensing limits of $5\times10^{-6}$ RIU and $1\times10^{-5}$ RIU for OP and PP, respectively. The darkest region corresponds to the observed error $1.7\times10^{-3}$ (standard deviation) due to lack of full optimization in the feedback controls, and therefore limited our direct measurement limit to ~$1.5\times10^{-5}$. We estimate the limits for a nonabsorbing overlayer (with a gaseous species analyte, for example) with OP and an optimized rotation stage (mechanical limits of ~$10^{-4}$ in angle) to be on the order $1\times10^{-6}$ which is shown with the lightest shading.

While peak position is typically determined more precisely, it is useful to introduce the following metric $$X_{\lambda,\theta} \equiv S_{\lambda,\theta}/\Gamma_{\lambda,\theta},$$

as a measure of the resolving power that facilitates comparisons of different sensors and interrogation methods. In the above equation, S is the sensitivity (i.e. derivative of resonance position with respect to index of refraction) and $\Gamma$ is the FWHM and the subscripts $\lambda(\theta)$ refers to wavelength (angular) interrogation, respectively. We experimentally determine $S_\lambda$~1022±8 nm-$RIU^{-1}$ and $S_\theta$~78.4±0.6 deg-$RIU^{-1}$ that yield values of $X_\theta$~850 $RIU^{-1}$ and $X_\lambda$~410 $RIU^{-1}$ with an air overlayer while these values are reduced to $X_\theta$~150 $RIU^{-1}$ and $X_\lambda$~120 $RIU^{-1}$ with water broadened transmission.

We have demonstrated a high resolution SPR sensor based on transmission through nanohole arrays. In these structures (and gratings in general), the propagation length may be reduced to specification and can therefore increase the relative system resolution (limit the crosstalk between channels). This leads to a design tradeoff: the sensitivity may be sacrificed for smaller interrogation volumes depending on the particular application. Some variations can be made based on the designs described in this application, including design of the periodic structure to enhance the absorption response by tuning the SPR to a molecular resonance of interest. In addition, one can break the in plane symmetry and use, for example, elliptical or chiral shaped holes to have polarization dependence even at the normal incidence. These results will help in designing future grating coupled surface plasmon resonance sensors, both in the transmission (a nanohole) and the traditional (reflection surface grating relief) geometries.

The following sections further describe polarization properties of nanohole arrays used in the optical sensing devices of this application. The surface plasmon polariton mediated resonant transmittance through square arrays of cylindrical holes in an optically thick metallic film can be isolated by means of polarization rotation. Transmittance data for co-polarized and cross-polarized cases are described accurately with Fano-type and pure Lorentzian lineshapes, respectively. This polarization control allows for changing the relative weights of resonant and non-resonant transmission mechanisms, thus controlling the shape and symmetry of the observed Fano-type lineshapes.

Excitation of surface plasmon polaritons (SPPs) in nanohole arrays produces resonant and "enhanced" transmission through subwavelength apertures, the nanoholes. Typically, scattering (reflection and transmission) coefficients of any periodic grating supporting a slow wave are characterized by resonant features, e.g. strong resonant peaks in the magnitude of the transmission coefficient through a perforated metal plate, which occur approximately when the wavevector of one of the diffraction orders matches that of a slow wave. These features are manifestations of so-called resonant Wood anomalies. Mathematically, these anomalies are evident through the presence of complex frequency/angular poles in the scattering coefficient for incident radiation with a given real frequency/angle. When the incident field frequency/angle is scanned through these poles, the scattering coefficient exhibits resonant behavior. In addition to these resonances, a non-resonant field component is always present as well. The superposition of the resonant and non-resonant components results in asymmetry in the shape of the scattering coefficients, resulting is so called Fano profiles, which depend on the relation between the magnitude and phase of the resonant and non-resonant components.

The relation between the resonant and non-resonant components depends not only on the structure parameters but also on the measured parameter provided by a specific experimental setup. Indeed, a linearly polarized field upon scattering from a doubly periodic nanohole array generates co- and cross-polarized components. Using an additional polarizer in the scattered field, referred to in the following analysis as an analyzer, allows control of the each of these components of the scattered field and thereby changes the shape of the measured transmitted field. Most of the utilized experimental setups implement measurements of co-polarized incident and scattered field components, thus limiting the observed lineshapes. The objective here is to demonstrate experimentally and analytically the dependence of measured intensity through a periodic array of sub-wavelength holes after analyzing the polarization state of the transmitted optical field for various input polarization states. The presented ideas and results have a wide applicability to the general theory resonant gratings. For example, typically the frequency dependence of the resonant scattering coefficients is associated with red shifted tails. The shape of the scattering coefficient magnitude depends on the relation between both the amplitude and the phase of the resonant and non-resonant components. Within this framework, we show that the entire polarization dependence drops out quite naturally. and the polarization properties of resonant scattering from a two-dimensional nanohole array in a metallic film. The shape of the resonant transmission depends on the polarization state of the incident field, the excited SPP mode, and the polarization state of the measuring apparatus. This property of a nanohole array allows for observation of both Fano-type and pure Lorentzian lineshapes.

As described above, the SPR condition in a nanohole array leads to enhanced transmittance mediated by its excitation on a single side of the metal film. When the phase matching condition is met, the incident field interacts strongly with the SPP and this interaction results in strongly enhanced transmission. The phenomena of enhanced transmission can be explained more rigorously as particular manifestations of so called resonant Wood anomalies that are also associated with Fano profiles. In the framework of the theory of resonant Wood anomalies, the transmission (scattering) coefficients are represented as a sum of resonant and non-resonant components. We consider the spectral transmittance through the 2-D nanohole array for excitation of SPP on one side of the film only. This assumption means that the frequencies of the lowest order SPP modes excited on the upper and lower interfaces of the metal-dielectric boundaries are well separated in frequency, and therefore there is no coupling between the SPP modes on the opposite sides of the metal film (i.e., under assumption that the coupling to higher order modes is weak).

The experimental samples are a 100 nm-thick aluminum film on a GaAs substrate perforated by a 2-D array of holes with diameters d ~350 nm and with periods a of 1.2, 1.4 and 1.6 μm. The total perforated area of 200×200 μm was used for measurements. The sample was first aligned normal to the beam axis and the azimuthal angle φ was set to a value of either 0 or π/4 corresponding to the Γ-X or Γ-M directions in the receprical lattice space. At each azimuthal angle, the polar angle θ (i.e., angle of incidence) was varied from 0 to 7π/36 rad (corresponding to about 35°). Measured dispersion for the three samples with various periods, a, is shown in FIG. 11A, displaying the unpolarized (i.e., polarizer/analyzer pair removed), zero-order transmittance for normalized frequency versus normalized in-plane wavevector in both the Γ-X and Γ-M directions. Data has been normalized by the hole area per unit cell and combined to give a full perspective on the SPP excitation conditions for a large characterization space. The maximum transmission of (~9% for a=1.4 μm, ~13% for a=1.2 μm) occurs at normal incidence for a slightly red shifted wavelength from that corresponding to a/λ=1.0.

The data is dominated by the asymmetric, Fano-type lineshape features, which correlate with resonant transmission by excitation of various SPP wave modes at the various orders (m,n). The essential feature to notice is that the SPP fields are excited at neither the maxima nor the minima of this curve; rather, the interference between the resonant and nonresonant components leads to the dispersive lineshape. For these samples, SPP modes on the air-metal (AM) interface are efficiently excited; the first order modes for the semiconductor-air interface occur at much lower frequencies, and the higher order modes that occur at these frequencies are clearly not discernable in these measurements. Dispersion curves shown in FIG. 11B are calculated for SPP excitation at the AM interface for a single period (a=1.4 μm) according to Eqs. (1-3) and including the frequency dependence of the dielectric constant of aluminum. These curves predict well the frequency of the SPP features for all of the data on the normalized frequency scale. More rigorous methods are required to theoretically determine the relative strength of the coupling as well as the absolute spectral shape of the various bound and propagating modes (i.e., diffraction orders). Qualitatively, however, there have been a number of studies that have succeeded in explaining the effects of the various geometric parameters on the spectral transmittance. The resonant transmission mechanism is based on coupling to an SPP mode, evanescent transmission through the below-cutoff waveguide hole, and scattering of radiation again from the hole array to produce propagating modes. The hole size, in the long wavelength limit, determines the scattering rate and hence the lifetime of the mode, and increasing size will tend to increase the linewidth of the transmitted radiation. We investigate the polarization dependence of the spectral transmittance of this resonant transmission mechanism more carefully in the next section.

A different nanohole array sample is used for more careful study of the resonant transmission mechanism. The sample is an array of holes in gold film on a silica glass substrate with the geometric parameters h~200 nm, d~200 nm, and a ~1.63

μm. The Ti adhesion layer of ~10 nm is also used to effectively suppress SPP fields on the gold-substrate interface. We consider the polarization dependence of a single resonant mode, [+1, 0]. A tunable laser with a spectral linewidth much narrower than the SPP resonant transmission linewidth is used to provide a probe laser beam in the spectral range of $\lambda$=1520-1570 nm. The parameter space of the measurements is indicated by the small, shaded regions in FIGS. 11A and 11B. For this sample, the film thickness is larger, the hole diameters are smaller, and the divergence of the beam is smaller, all of which leads to much narrower measured linewidths than shown in illustrated in FIGS. 12A and 12B.

FIGS. 12A and 12B show the polarization dependent spectral transmission for a fixed value of $\theta=\pi/90$. Data in FIG. 13B is the same as in FIG. 12A and is normalized along each $\psi^A$ to the maximum of each scan in the radial direction (normalized frequency, a/λ) for viewing the salient properties of the transmittance. The incident field polarizer angle is set to an angle $\psi^P=\pi/4$, and the output field polarization analyzer angle, $\psi^A$ is varied from 0 to $2\pi$ in increments of $\pi/36$. In FIG. 12A, the measured transmittance exhibits a Malus' law-type $\cos^2\psi^A$ dependence across the entire spectral range. This data has been smoothed to remove the effects of reflections from the substrate (which had no anti-reflection coating). To see the underlying structure, FIG. 12B shows the normalized data along the radial (i.e., normalized frequency a/λ) direction for each value of $\psi^A$ to the maximum of each scan in the radial direction.

The transmission maximum is clearly observed to vary with $\psi^A$—most notably, the white, maximum value, is not circular (see FIG. 3b). This is most clearly evident at $\pi/2$ ($3\pi/2$), where there is a discontinuity in the transmission maximum. Qualitatively, this is a result of a shift due to the interaction of the discrete state resonance with the continuum. Moreover, the transmission is never extinguished because of effective polarization rotation by the resonant transmission mechanism. The surface wave is excited by a projection of the incident polarized field, and the propagating surface field interacting with the nanohole array creates a reradiated field which is again projected onto the analyzer. The nonresonant background contribution can be effectively suppressed and in this case the resonant term can be isolated and investigated independently. The above techniques for the specific case of a single [+1,0] type order can be applied to other various resonant orders of the same nanohole array or more generally to periodic structures of different symmetries.

While this specification contains many specifics, these should not be construed as limitations on the scope of what being claims or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Only a few implementations are disclosed. However, other variations and enhancements may be made.

What is claimed is:

1. An optical sensing device, comprising:
    a nanohole array comprising a substrate and a metal layer formed on the substrate to include an array of holes arranged in a periodic two-dimensional pattern and to be in contact with a sample under measurement, each hole having a dimension less than one wavelength of probe light to which the nanohole array is responsive to produce surface plasmons at an interface of the metal layer and the sample under a surface plasmon resonance condition;
    an input optical module to direct a collimated input optical probe beam at the wavelength of the probe light to the nanohole array, the input optical module comprising an optical polarization control unit operable to control an input optical polarization of the collimated input optical probe beam incident to the nanohole array; and
    an output optical module to receive an optical output produced by the surface plasmons at the interface between the metal layer and the sample, the output optical module comprising an output optical polarizer to select light in the optical output at a selected output polarization for optical detection,
    wherein the input optical module further comprises an actuator to control an incident angle of the collimated input optical probe beam to achieve the surface plasmon resonance condition.

2. The device as in claim 1, wherein the optical polarization control unit and the output optical polarizer are configured to be orthogonal to each other in polarization to produce a Lorentzian spectral profile in the optical output that transmits through the output optical polarizer.

3. The device as in claim 1, wherein the output optical module comprises:
    an optical sensing device to receive and capture an image of the optical output that transmits through the output optical polarizer; and
    an optical imaging unit placed in an optical path between the nanohole array and the optical sensing device to image the nanohole array onto the imaging device.

4. The device as in claim 3, wherein the optical sensing device is a camera and the optical imaging unit comprises two lenses in a 4f lens configuration.

5. The device as in claim 1, wherein the input optical module comprises a tunable light source to control at least one of the wavelength and the amplitude of the collimated input optical probe beam to achieve the surface plasmon resonance condition.

6. The device as in claim 1, wherein the nanohole array comprises a microfluidic channel in contact with the metal film to support a fluid sample under measurement.

7. The device as in claim 6, wherein the microfluidic channel is formed from a polymer.

8. The device as in claim 1, wherein the nanohole array comprises a plurality of parallel microfluidic channels in contact with the metal film and each microfluidic channel supports a respective fluid sample under measurement.

9. The device as in claim 1, wherein the optical output produced by the surface plasmons at the interface between the metal layer and the sample is an optical transmission through the metal film and the sample and,
    wherein the input and output optical modules are located relative to the nanohole array to direct the collimated input optical probe beam to the nanohole array and to receive the optical output from the nanohole array, respectively, on opposite sides of the nanohole array.

10. The device as in claim 1, wherein the optical output produced by the surface plasmons at the interface between the metal layer and the sample is an optical reflection by the metal film,
wherein the input and output optical modules are located relative to the nanohole array to direct the collimated input optical probe beam to the metal film of the nanohole array and to receive the optical output reflected from metal film of the nanohole array so as to direct the collimated input optical probe beam and receive the optical output on a same side of the nanohole array.

11. The device as in claim 1, wherein each hole in the metal film of the nanohole array is spatially anisotropic in shape.

12. The device as in claim 11, wherein each hole in the metal film of the nanohole array is elliptical.

13. The device as in claim 1, wherein the metal film comprises at least one of Ag, Au, Al and Cu.

14. The device as in claim 1, wherein the polarization control unit in the input optical module comprises first and second optical polarizers and a quarter wave plate between the first and second optical polarizers.

15. The device as in claim 1, wherein the output optical modulator comprises a quarter wave plate or a liquid crystal modulator to filter the optical output that is received by the output optical polarizer.

16. The device as in claim 1, wherein the metal film of the nanohole array is functionalized with a biomolecular recognition element.

17. The device as in claim 1, wherein each hole in the nanohole array is a through hole in the metal film.

18. The device as in claim 1, wherein each hole in the nanohole array penetrates a part of the metal film without penetrating through the metal film.

19. The device as in claim 1, further comprising a mechanism to adjust a relative orientation between the input optical module and the nanohole array to adjust an incident angle of the collimated input optical probe beam at the nanohole array.

20. The device as in claim 1, wherein the nanohole array further comprises different sample areas in contact with different samples under illumination by the collimated input optical probe beam; and
wherein the input optical module is configured to produce different collimated optical probe beams to simultaneously illuminate the different sample areas.

21. The device as in claim 20, wherein the different sample areas are respectively functionalized with different biomolecular recognition elements on the metal film.

22. An optical sensing method, comprising:
providing a nanohole array comprising a metal layer and an array of holes arranged in a periodic two-dimensional pattern to be in contact with a sample under measurement, wherein each hole has a dimension less than one wavelength of probe light to which the nanohole array is responsive to produce surface plasmons at an interface of the metal layer and the sample under a surface plasmon resonance condition;
directing a collimated input optical probe beam at the wavelength of the probe light to the nanohole array under the surface plasmon resonance condition to excite surface plasmons at the interface of the metal layer and the sample;
directing light in an optical output produced by the surface plasmons at the interface between the metal layer and the sample in a selected output polarization into a camera;
processing an image captured by the camera to extract information of the sample; and
controlling an incident angle of the collimated input optical probe beam to achieve the surface plasmon resonance condition.

23. The method as in claim 22, further comprising:
controlling input polarization of the collimated input optical probe beam and the selected output polarization for the light captured by the camera to be orthogonal to each other to produce a Lorentzian spectral profile in the light captured by the camera.

24. The method as in claim 22, further comprising:
controlling at least one of the wavelength and the amplitude of the collimated input optical probe beam to achieve the surface plasmon resonance condition at the interface between the metal layer and the sample.

25. The method as in claim 22, further comprising:
functionalizing the metal layer with a biomolecular recognition element to target selected samples particles for measurement.

26. The method as in claim 25, further comprising:
applying a molecular fluorescent tag in the sample to enhance the measurement specificity.

27. The method as in claim 22, further comprising:
functionalizing different sample areas in the metal layer with different biomolecular recognition elements, respectively, to target different selected samples particles for measurement.

28. The method as in claim 27, further comprising:
controlling the collimated input optical probe beam to produce different collimated optical probe beams to simultaneously illuminate a plurality of the different sample areas to simultaneously measure different samples attached to the different sample areas.

29. The method as in claim 22, further comprising:
attaching at least one microfluidic channel to the metal film to supply a liquid sample to be measured by the collimated input optical probe beam.

30. The method as in claim 22, further comprising:
using the collimated input optical probe beam to produce different collimated optical probe beams to simultaneously illuminate different sample areas on the nanohole array to simultaneously measure the different sample areas.

31. An optical sensing device, comprising:
a nanohole array comprising a metal layer with a two-dimensional array of holes configured to interface with a sample under measurement and to support surface plasmon under excitation of probe light, each hole having a dimension less than one wavelength of the probe light;
an input polarization control unit to control input polarization of an input optical probe beam of the probe light incident to the nanohole array;
an output optical polarizer to receive signal light which is transmission of the input optical probe beam through the nanohole array and the sample to select a polarization of the signal light for optical detection,
wherein the input polarization control unit and the output optical polarizer are configured to be orthogonal to each other in polarization; and
a positioning stage to hold the nanohole array and to adjust the orientation of the nanohole array relative to the input optical probe beam to achieve a surface plasmon resonance condition at an interface between the metal layer and the sample.

32. The device as in claim 31, wherein the nanohole array comprises a microfluidic channel in contact with the metal film to support a fluid sample under measurement.

33. The device as in claim 31, wherein the nanohole array comprises a plurality of parallel microfluidic channels in contact with the metal film and each microfluidic channel supports a respective fluid sample under measurement.

34. The device as in claim 31, wherein each hole in the metal film of the nanohole array is spatially anisotropic in shape.

35. The device as in claim 31, wherein the metal film of the nanohole array is functionalized with a biomolecular recognition element.

36. The device as in claim 31, wherein the nanohole array further comprises different sample areas in contact with different samples under illumination by the collimated input optical probe beam; and
the device further comprises an input optical module to produce different collimated optical probe beams to simultaneously illuminate the different sample areas.

37. The device as in claim 36, wherein the different sample areas are respectively functionalized with different biomolecular recognition elements on the metal film.

38. The optical sensing device as in claim 31, comprising a tunable light source to control at least one of the wavelength and the amplitude of the input optical probe beam to achieve the surface plasmon resonance condition.

39. An optical sensing device, comprising:
a substrate;
a metal layer formed on the substrate and patterned to comprise a two-dimensional array of holes configured to interface with a sample under measurement and to support surface plasmons under excitation of probe light, each hole having a dimension less than one wavelength of the probe light;
a plurality of microfluidic channels formed in contact with the metal film, wherein each microfluidic channel supports a respective fluid sample under measurement; and
an input optical module to direct a collimated input optical probe beam at the wavelength of the probe light to the nanohole array, the input optical module comprising
an optical polarization control unit operable to control an input optical polarization of the collimated input optical probe beam incident to the nanohole array, and
an actuator to control an incident angle of the collimated input optical probe beam to achieve a surface plasmon resonance condition at an interface between the metal layer and the sample.

40. The device as in claim 39, further comprising:
an output optical module to receive an optical output produced by the surface plasmons at the interface between the metal layer and the sample, the output optical module comprising an output optical polarizer to select light in the optical output at a selected output polarization for optical detection; and
a camera positioned to capture an image of the selected light that transmits through the output optical polarizer.

41. The device as in claim 40, wherein the optical polarization control unit and the output optical polarizer are configured to produce a Lorentzian spectral profile in the optical output that transmits through the output optical polarizer.

42. The device as in claim 39, wherein each hole in the metal film of the nanohole array is spatially anisotropic in shape.

43. The device as in claim 39, wherein the metal film of the nanohole array is functionalized with a biomolecular recognition element.

44. The device as in claim 39, wherein the nanohole array further comprises different sample areas in contact with different samples; and
wherein the input optical module is configured to produce different collimated optical probe beams to simultaneously illuminate the different sample areas.

45. The device as in claim 44, wherein the different sample areas are respectively functionalized with different biomolecular recognition elements on the metal film.

46. The device as in claim 39, wherein the input optical module comprises a tunable light source to control at least one of the wavelength and the amplitude of the collimated input optical probe beam to achieve the surface plasmon resonance condition.

* * * * *

UNITED STATES PATENT AND TRADEMARK OFFICE
CERTIFICATE OF CORRECTION

| | | |
|---|---|---|
| PATENT NO. | : 8,094,314 B2 | Page 1 of 1 |
| APPLICATION NO. | : 12/091051 | |
| DATED | : January 10, 2012 | |
| INVENTOR(S) | : Kevin Tetz, Lin Pang and Yeshaiahu Fainman | |

It is certified that error appears in the above-identified patent and that said Letters Patent is hereby corrected as shown below:

IN THE SPECIFICATIONS:

At column 1, line 15, please delete the entire heading and paragraph and insert the following amended heading and paragraph:

-- STATEMENT REGARDING FEDERALLY SPONSORED RESEARCH OR DEVELOPMENT

This invention was made with government support under contract numbers FA9550-04-1-0285 and FA9550-04-1-0417 awarded by U.S. Air Force Office of Scientific Research (AFOSR) and under contract number ECS-0403589 awarded by National Science Foundation (NSF). The government has certain rights in the invention. --

Signed and Sealed this
Twenty-ninth Day of May, 2012

David J. Kappos
*Director of the United States Patent and Trademark Office*